United States Patent
Bengsch et al.

(10) Patent No.: US 6,339,950 B1
(45) Date of Patent: Jan. 22, 2002

(54) PROCESS FOR DETERMINING THE NUMBER OF COMPONENTS IN PEAKS, BANDS, AND SIGNALS OF CHROMATOGRAMS, ELECTROGRAMS, AND SPECTROGRAMS

(75) Inventors: Eberhard Bengsch, Munich; Jürgen Polster, Freising; Antonius Kettrup, Arnsberg, all of (DE)

(73) Assignee: GSF Foschungszentrum für Umwelt und Gesundheit GmbH, Oberschleissheim (DE)

( * ) Notice: Subject to any disclaimer, the term of this patent is extended or adjusted under 35 U.S.C. 154(b) by 0 days.

(21) Appl. No.: 09/474,212

(22) Filed: Dec. 29, 1999

Related U.S. Application Data

(63) Continuation-in-part of application No. PCT/EP98/03272, filed on Jun. 2, 1998.

(30) Foreign Application Priority Data

Jun. 30, 1997 (DE) .......................................... 197 27 879

(51) Int. Cl.[7] ......................... B01D 15/00; G01N 21/25; G01N 30/02
(52) U.S. Cl. ..................................... 73/23.36; 73/23.35
(58) Field of Search .............................. 73/23.25, 23.36

(56) References Cited

U.S. PATENT DOCUMENTS 5,596,135 A    1/1997   Mito et al. .................. 73/23.35

FOREIGN PATENT DOCUMENTS

| EP | 0 294 121 | 12/1988 |
| EP | 0 486 030 | 5/1992 |

OTHER PUBLICATIONS

J. Polster et al. "New Methods For Spectrometric Purity Analysis In Chromatography", *Journal of Chromatography A*, 1998.

Primary Examiner—Daniel S. Larkin
(74) Attorney, Agent, or Firm—Klaus J. Bach

(57) ABSTRACT

In a process for determining the number of components involved in the formation of peaks, bands, and signals which are obtained in spectrograms where energy-correlated measurement values, such as extinctions, increase and decrease as a function of an evolving parameter, such as time, four different measurement values with at least three evolving parameter values are determined, three differences are formed from the four energy-correlated measurement values on the basis of the same evolving parameter, two quotients are formed from the respective differences and the two quotients are plotted over one another in a diagram, whereby a point is obtained if one component is responsible, a straight line is formed if two components are responsible and a curve is formed if more than two components are responsible for the formation of the peaks, bands, or signals.

7 Claims, 2 Drawing Sheets

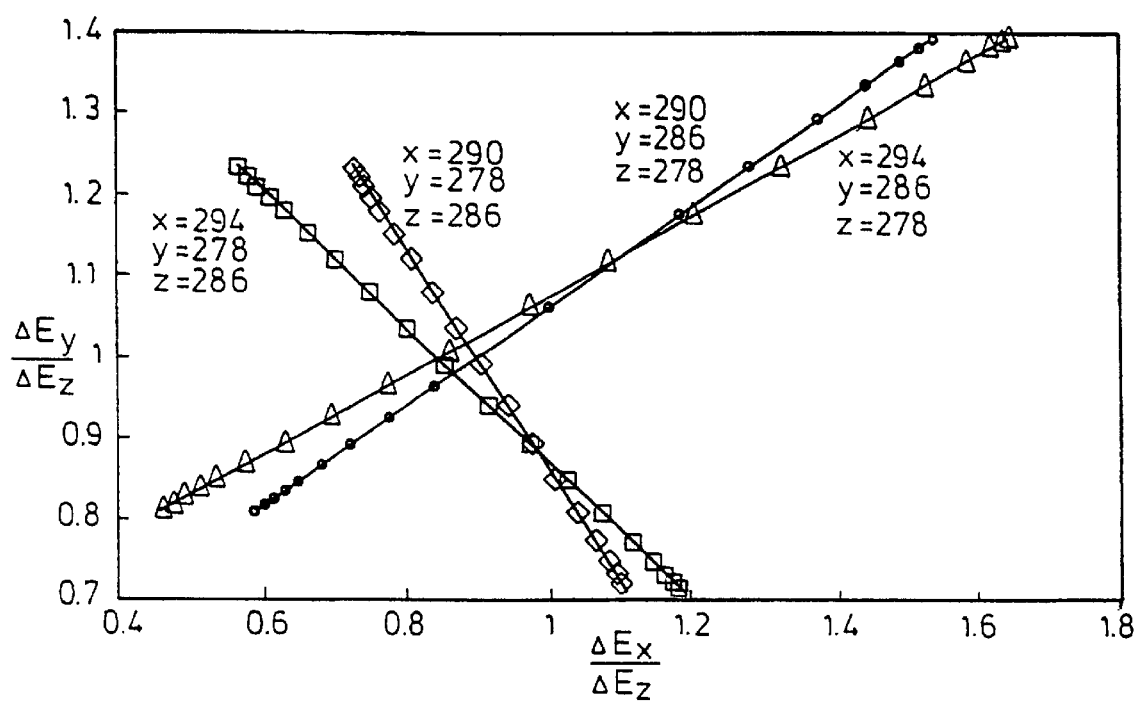

US 6,339,950 B1

PROCESS FOR DETERMINING THE NUMBER OF COMPONENTS IN PEAKS, BANDS, AND SIGNALS OF CHROMATOGRAMS, ELECTROGRAMS, AND SPECTROGRAMS

This is a continuation-in-part application of international patent application PCT/EP98/03272 filed Jun. 2, 1998 and claiming the priority of German application 197 27 879.5 filed Jun. 30, 1997.

BACKGROUND OF THE INVENTION

The invention resides in a process for determining the number of components in peaks, bands, and signals of chromatograms, electrograms, and spectrograms of all types obtained for analysis and substance separation wherever energy-correlated measurement values as a function of an evolving parameter appear and again disappear.

Modern analysis and separation techniques for any type of material proceed more and more toward a full automatization of the procedure from the sampling up to providing the desired final results. In such a procedure, the process scheme is repeated identically independently of the type of analysis. This is true generally for the locating and the identification of the material, but also for the sequencing of proteins, nucleic acids, carbohydrates, lipids, etc.: Progressive attachment, distribution on the basis of individual travel behavior and desorption of substances on various carrier materials and the subsequent substrate detection by way of dispositives sensitive thereto and preferably having a spectroscopic nature.

Experience has shown that, in addition to the homogeneous detection peaks which are generated by a single pure component (=100% peak purity), in other signals the spectral contributions of two or several components are mixed together (=mix-peaks).

The main reasons herefor are:

Quasi-identity of the components to be separated, for example, families of effective substances occur in the natural material chemistry. The individual components differ only slightly from one another.

The use of an unadapted separation process, which permits several components to appear in the same detection zone.

Peak determination under less than optimal conditions for the detection.

The peak purity and, if applicable, the number of spectrally overlapping components could not be easily recognized and utilized so far apparatus-logistically. When such uncertainties occur, the reaction of the apparatus is delayed and the final results are doubtful.

Highly developed measuring and separating processes, which are optimized in any other way, are limited in their efficiency by this general uncertainty factor.

U.S. Pat. No. 5,596,135 A discloses a process, which is based on the extinction difference diagrams. With this process, it can be determined whether a peak in a chromatogram is caused by one or several components. If there is more than one component, the number of components cannot be clearly determined.

EP 0 486 030 A discloses a similar method, which is based, however, on extinction diagrams.

Furthermore, EP 0 294 121 A discloses a method, wherein the number of components of a mixture can be determined using a mathematically complicated main component analysis (on the basis of a matrix with the determination of individual values and vectors).

It is the object of the present invention to provide a simple method by which the number of components in a mixture can be clearly determined.

SUMMARY OF THE INVENTION

In a process for determining the number of components involved in the formation of peaks, bands, and signals which are obtained in spectrograms where energy-correlated measurement values, such as extinctions, increase and decrease as a function of an evolving parameter, such as time, four different measurement values with at least three evolving parameter values are determined, three differences are formed from the four energy-correlated measurement values on the basis of the same evolving parameter, two quotients are formed from the respective differences and the two quotients are plotted over one another in a diagram, whereby a point is obtained if one component is responsible, a straight line is formed if two components are responsible, and a curve is formed if more than two components are responsible for the formation of the peaks, bands, or signals.

The method permits a precise and rapid determination of the number of components in peaks, bands, and signals, which are obtained for the analysis and component separation in all kinds of spectrograms, where energy correlated measurement values increase decrease as a function of an evolving parameter. The plurality of measurement values are derived from a particular such parameter value and differently energy-correlated so as to form characteristic geometric figures, in which the original evolving parameter is not contained. The figures obtained are reduced, depending on their complexity, in steps, first to straight lines and then to points. In this way, the number of the components involved in the formation of the peaks and consequently the composition of the whole spectrogram and also of the component mixture to be examined and/or separated is obtained in a simple manner.

In a preferred embodiment of the invention, instead of the energy-correlated direct-measurement values, the differences thereof or quotients thereof or even the quotients of the differences are placed in relation to one another in a simple way or in multiple ways. It becomes progressively possible thereby to extract 2, 3, 4 or more individual components from the peak and to identify and separate them. Also, the areas in a particular parameter range surrounded by the respective energy measurement values may be placed in relation to each other as integrals, whereby geometric figures are provided from which the peak compositions and analysis results can be obtained. This additionally improves the signal/noise ratio with a corresponding gain in sensitivity of the respective technical method.

A variant of the process for determining the number of components of spectrograms, wherein the structures are energy-correlated measurement values, which appear and disappear as a function of an evolving parameter and which consequently change with the parameter comprises the following process steps:

a) determining at least two different function values of measurement values, wherein each measurement value is assigned to a different energy, based on the same parameters, b) determining at least two additional function values with the same energy correlation as in step a) based on at least two additional different parameters so that, for each energy value, there are at least three function values with three different parameters, c) interpreting the function values belonging to the various energies as a parameter representation of an at least two-dimensional curve, and d) evaluating the curve on the basis of predetermined criteria. The measurement values may be extinction values and the parameter may be time.

It is known that the separation and analysis processes of component mixtures operate, in their decisive phase, on the basis of registering those detection peaks, which are the result of spectroscopic measurement data. This is true for example for the HPLC-, the liquid-, the gas, the thin layer-, the affinity-, the adsorption-, and ion exchange chromatography, as well as for electrophoretic processes, and for any analog separation procedure.

From a simple and efficient elimination of the above-characterized central problem, an important technical advance for all automated separation and analysis processes can be expected.

The problems described earlier are eliminated by the process according to the invention. The process is direct, simple, free of delays and significant. It operates with a minimum of evaluation needs and leads to clear results.

The solution for the problem is centered about the detection peak.

Following the original classic separation processes, the number of analytical and preparative component separation procedures by way of chromatography has constantly increased. Alone in Europe, 100,000 such apparatus are in operation in all research and other professional areas. It can be assumed that this trend continues. Most detection and measurement methods in operation register the spectroscopic data dependent on the retention time and/or a travel behavior. The chromatograms obtained in this way are then used for the identification and the quantitative determination of individual components. It has been of utmost importance in these procedures that various components could be physically separated from each other to provide homogeneous individual signals.

With each chromatographic separation method on the basis of spectroscopic measurement methods, the basic question comes up again and again: How many components have a spectroscopic influence on the individual peaks of the chromatograms?

Because of the great importance of the individual contribution of each component to the more or less complex chromatogram, a large number of methods for the individual characterization of the components has been developed. The large efforts which have been expended in this respect and which are still being expended show that this problem has not been solved satisfactorily in spite of the continuing efforts.

A solution for this problem is of great importance for all measuring and separation methods, which are based on the registration of time-dependent signals. This importance applies also to any other method, wherein a signal appears and again disappears. Like in the chromatography, the individual separated bands can be examined spectroscopically in a time-dependent and position dependent manner also for example in a continuing electrophoresis process.

The drifting of basis lines and the partial disappearance of weak signals in noise are additional complication parameters for which substantial improvements are to be expected from the process according to the invention.

For concentrations at the detection limits, for example, at the sequencing limit of proteins the question is: Is it a real peak, a noise peak, an impurity peak, or a mixture of those?

A solution to these problems requires a new way of analyzing and treating detection peaks and their incorporation, in a reasonable manner, in a preferably fully automated over-all process.

For the peak analysis diode array, spectrometers are preferably used in the HPLC and the electrophoresis in the UV-VIS range. In this way, it is possible with today's powerful computers to analyze chromatograms and electrograms spectrally down to the millisecond range. The 3D chromatograms and electrogams (extinction versus wavelength versus retention time or, respectively, an electrochemical parameter) registered in this way, are then generally subjected to a complicated numerical analysis. As examples, in this regard the following methods were developed.

Surface centerpoint analysis peak deconvolution vertical line and peeling method spectra comparison using chemometric procedures peak purity index rationing (formation of ratios)

Most of these methods are complicated and expensive and are integrated in commercial apparatus which makes them very expensive. For example, multiple-variation methods or curve analyses on the basis of Gauss-distribution curves are utilized. All these methods however, have serious disadvantages:

The user can utilize these methods generally only schematically and routinely without any modification since these methods generally permit no changes as they are offered in the form of rigid uncontrollable "black-box" units, which cannot be changed.

The user cannot decide which results should be weighted more heavily when different procedures show contradicting results.

Numerical artifacts and problems with bad mathematical conditions are difficult to recognize during routine applications.

The experience of the user cannot be entered into the evaluation: the instrument cannot learn.

The extinction (E), extinction differences (ED), and extinction quotient (EDQ) diagrams were introduced in 1968 for the theory of the reaction kinetics. (H Mauser, Publication Naturforsch., 23b (1968), pages 1025–1030).

Herein, it was shown in connection with reacting chemical systems including some short-lived intermediates that, by plotting the timely subsequent extinction values at a wave length ($\lambda i$) on the basis of the corresponding values at the same time at another wavelength ($\lambda j$), while eliminating the time parameter, characteristic curves are obtained. Such diagrams $E_{\lambda i}$ versus $E_{\lambda j}$ are called extinction diagrams (=E diagrams).

If the differences between the extinction values are determined and plotted over the corresponding differences of other wave lengths, extinction difference diagrams (-ED-diagrams) are provided in the same manner. For forming the differences, extinction values at different reaction phases are utilized.

If corresponding differences of different wavelengths are divided by one another, extinction difference quotient diagrams (=EDQ-diagrams) are generated. Such differences represent determinants of the first grade. It is possible to continue with the system of determinants to the grades 2, 3 . . . to s.

Inspite of the existence of such diagrams in the theoretical field of kinetics since more than 25 years and the long-time efforts of the apparatus manufacturers to overcome the main weak point of peak interpretations, for example in the chromatography, the above diagrams have not been used so for rationalizing the processing of the flood of data supplied to the analysis apparatus. The reason herefor is probably that the kinetic examinations of reaction mechanisms and the chromatographic separation procedures for component mixtures have nothing in common. They serve completely different purposes. Reaction-kinetic theories and the practical problems of separation of compound mixtures are disciplines, which are widely separated. The introduction of E-diagrams into the separation of components was apparently not obvious.

It has now been found that, with the use of the E-, ED-, EDQ-diagrams, and particularly the integral extinction diagrams (=iE diagrams), which were specifically developed for the process according to the invention and which will be described below in connection with the analysis of the spectra, the substance coordination and determination in chromatographic separation processes becomes surprisingly extremely simple and comprehensible. It becomes instantly possible to determine whether there is a mono-peak, a double peak, or a multi-peak and the respective number of components involved, if applicable. Also, a noise peak included in the peak can be recognized. Complicated logistic auxiliary units become therefore superfluous. The total instrumentation is simplified, more reliable, and less expensive. Furthermore, the time required for obtaining an analysis result is substantially reduced.

The speed, the reliability, and the costs of the analysis are improved in a spectacular way.

In the chromatography, the detection method is based on the fact that the recorded spectra change dependent on the retention time. By plotting the extinctions of various wave lengths $E_{\lambda,i}(t)$ resulting from the same retention times (t) with respect to each other, characteristic geometric figures are obtained which provide the desired characterization concerning the authenticity and the complexity of the signals examined. Such figures are points, straight lines, areas, or multidimensional shapes (polyhedra). Starting at a peak extremity having low E values, the curves evolve in the E diagram along such figures up to a reversal point with maximum E values and return to the original point in the E-diagram at the other peak extremity. The diagram formed in this way is called extinction space. The retention time generating the diagram is not contained therein any longer.

With the introduction of the simplified chromatographic analysis and separation process according to the invention a long-time need is satisfied. Purity, or respectively, multiplicity of the peaks is obtained in a most simple manner.

The invention may also be used in connection with any other process, wherein signals appear and disappear by means of time—or space—evolving parameters (for example, NMR, absorption—or reflexion spectroscopy of test carrier materials, double wave spectroscopy, fluorescence spectroscopy, optical rotation dispersion circular dichroism).

Before the development and an exemplary application of the various diagrams of the invention will be described, the capability is schematically shown in the following tables:

a) signal peaks with one or two components cover most of the chromatographic problems. They can be differentiated instantly using E- and EP diagrams.

TABLE 1

| Diagrams | Resulting Curve | Number of components determined |
| --- | --- | --- |
| E, ED | Straight Line | 2 or more |
| E, ED | curve | | b) The recognition and the treatment according to the invention of multi-component signals using further developed programs is possible.

Table 1 is expanded as a result according to the following scheme:

TABLE 2

| Diagram | Resulting Curve Shape | Number of Components Determined |
| --- | --- | --- |
| EDQ | Point | 1 |
| Quotients of Determinants of the Grade 1 | Straight line | 2 |
| | Curve | 3 or more |
| EDQ grade 2 | Point | 2 |
| | Straight Line | 3 |
| | Curve | 4 or more |
| EDQ Grade s-1 | Point | S − 1 |
| | Straight Line | S |
| | curve | S + 1 or more |

Embodiments of the invention will be described below on the basis of the accompanying drawings.

Figure 1:
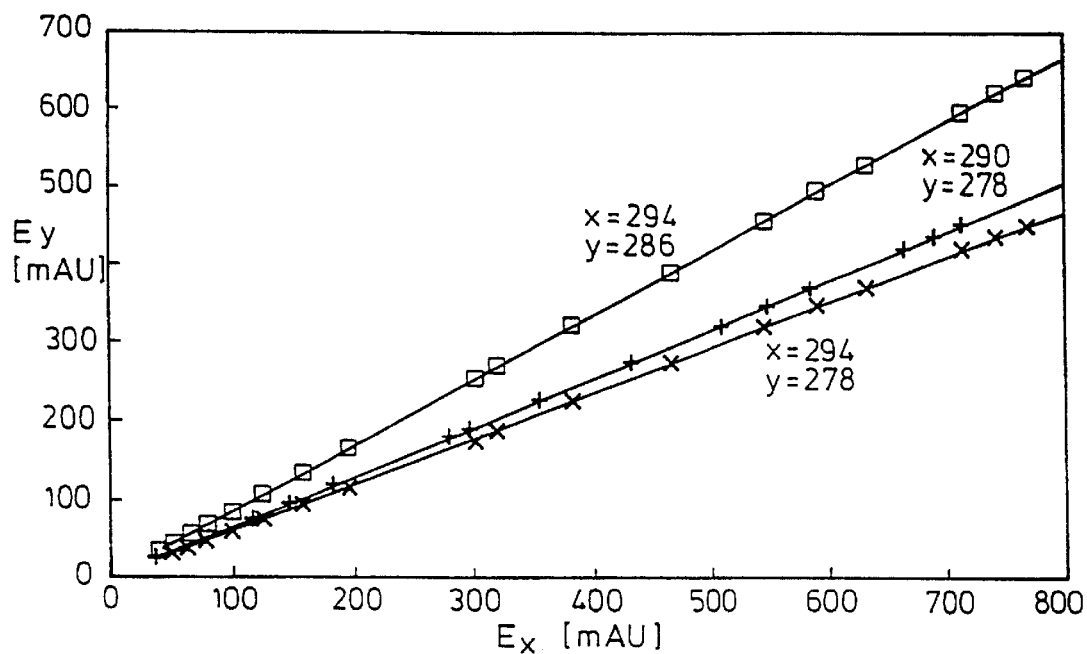
FIG. 1 shows an extinction (E) diagram including three different straight lines.

I. Setup of E-, ED-, integral E-, and integral ED- diagrams.

For detection purposes, in the chromatography, spectra are recorded in the UV-VIS range mostly in a wavelength ($\lambda$) dependent manner at different retention times (t). In the E diagram, the extinctions measured at given t values are plotted for various wave lengths ($\lambda i, \lambda j$), that is, $E_{\lambda,i}(t)$ versus $E_{\lambda,j}(t)$ or, simplified $E_i(t)$ vs. $E_j(t)$.

For the recorded spectra, usually the validity of the generalized Lambert-Beer-Bouguer law is assumed:

$$E_\lambda = d \sum_{i=1}^{S} \varepsilon_{\lambda_i} c_i(t)$$

(d=layer thickness of the measuring space of a solution, gas or the electrophoresis matrix $E_{\lambda,i}$=Extinction coefficient of the component i; $C_i$=concentration of i; S=maximum number of absorbing components which may contribute to the peak).

In extinction difference (ED) diagrams, the respective plotting points are developed:

$\Delta E_{\lambda,i}(t)$ vs. $\Delta E_{\lambda,j}(t)$ or simplified $\Delta E_i(t)$ vs $\Delta E_j(t)$ It applies:

$\Delta E_{\lambda,i}(t) = E_{\lambda,i}(t) - E_{\lambda,i}k \; E_{\lambda,i}k \; k=reference \; value$ While $\Delta E_{\lambda,j}$ and $E_{i,j}$ for the wave lengths i and j are time dependent values, the values $E_{i,j}k$ are, in the case of a constant spectral background (there is no drift of the wave-dependent basis lines), constants. For $E\lambda_i j k$ generally each $k^{th}$ measurement value (k=0.1, wherein k=0 represents the original value provided by the eluation means) can be used. However, preferably, in accordance with the invention, the initial measurement values ($E_{i}j_0$ with k=0 should be used or measuring points in the area of k=0.

If there is "peak purity" that is only one component (s=1) is to be analyzed spectroscopically in the peak of the chromatogram, straight lines are obtained in the E- and ED-diagrams. As a result, all single component signals of a chromatogram are immediately recognized, are separated from the inhomogeneous peaks and passed on to a quantitative evaluation.

Measuring example for mono-peaks.

In an exemplary embodiment of the process according to the invention, chlorogen acid (1.3 mg/ml) was dissolved in methanol, was sprayed onto a $C_{18}$-HPLC column, and washed with methanol (40° C.) and water (with 1% acetic acid). The chromatograms recorded with the aid of a UV-VIS diode array spectrometer at 250 to 400 nm were evaluated on the basis of E-diagrams. For the example of the mono peak given herein, clearly straight lines were necessarily obtained (FIG. 1).

In order to ensure that the homogeneity extends over the whole geometry of the peak, the extinctions of various wave lengths must be combined whereby a series of straight lines is obtained. In this way, the peak is confirmed as a mono peak.

Starting at the beginning of the peak with low extinction values, such a straight line is so formed that, from the coordinate origin of the diagram, the points are plotted in the direction of higher E values up to a culmination point from where they return along the same straight line.

The almost non-existing deviation of the measuring points forming the straight line in FIG. 1 is an indication of the precision of the process according to the invention.

Performance of the process:

Independently of the peak form (Gauss bell curve, Poisson distribution, and others), straight lines are obtained in the E- and ED-diagrams, whenever the number of the components contributing to form the peak is $s \leq 1$. The peak is pure and is not disturbed by any other component. The precision of the process is a result of the fact that the process is totally independent of the otherwise highly disturbing fading behavior (=asymptotic return to the original value) of the respective peak. In this way, a main disturbance factor of present chromatographic and other detection processes is eliminated in a simple manner.

The process provides for the simplest way of determining peak purity, which has been developed so far. It is also highly sensitive. Even the smallest systematic deviations can be recognized as significant. Mathematical manipulations are non-existent except for elementary operations, such as the formation of differences (ED diagram) quotients (EDQ-diagram) and/or of integrals in the diagrams to be below described iE-Diagrams.

The process includes no vague logistic operations and, as a result, is fully transparent for the user. The process requires a user to have only a minimum of basic knowledge of spectroscopy. There is no need for complicated mathematical procedures or chemo-metric methods and the instrumentation associated therewith.

In praxis and for routine measurements, the wavelengths $\lambda_1$ and $\lambda_i$ should be so selected that they are distributed in the recorded spectra as widely as possible. In this way, a field with distinct changes of the extinction is covered and a clear result is obtained. Preferably, the whole detection area is covered in this way; however, five wavelengths are already sufficient. A better result is achieved, however, if ten or more wavelengths are used.

Integral diagrams for high accuracy detection techniques and border line cases:

As already pointed out, the peaks are detected increasingly using ultra-fast diode array spectrometers. The classic spectral photometers, which record by the use of photomultiplyers, are more and more displaced. However, a disadvantageous signal/noise ratio (S/R) must be accepted. The following solution of the object of the invention includes the compensation of an unfavorable S/R ratio for example with diode array spectrometers. This is achieved by a further development of the invention: Instead of the E-and ED-diagrams described earlier the corresponding integral constructs are established and are fed into the automated analysis process.

By integrally combining the signals from several diodes, in the most simple case, the surfaces under the respective E-λ curves can be determined depending on the retention time by simple summing up of the signal trapezoid surfaces which form the signal surface integral. In this way, or by other common numerical methods, integrals of the form $$\int_{\lambda_1}^{\lambda_2} E_\lambda(t)d\lambda$$

Can be determined precisely rapidly and in a very simple way. In this way, the so-called integral extinction—(iE) diagrams are constructed as follows:

$$\int_{\lambda_1}^{\lambda_2} E_\lambda(t) \cdot d\lambda \text{ vs. } \int_{\lambda_3}^{\lambda_4} E_\lambda(t) \cdot d\lambda$$

It is possible that $\lambda_2=\lambda_3$ or $\lambda_1=\lambda_3$. In practice for the integration limits a wavelength range, $(\Delta\lambda=\lambda_2-\lambda_1=\lambda_4-\lambda_3)$ in the size of about 4–10 nm in the VV-VIS area was found to be advantageous. The iE diagrams so constructed result in the same statements as the E diagrams, but the precision is increased.

There is strong peak unity (s=1) if the iE diagrams generate straight lines. The use of integral iE diagrams provides for clear results also if the signal/noise ratios are very unfavorable. As a result, chromatograms, which are not useable in the classical detection procedures, will still have clear results.

Such an application resides for example in the sequencing of peptides, proteins and protein fractions by way of Edmann-Abbau where, with increasing distance from the N terminal origin point, the signals finally disappear in the noise whereby further sequencing becomes impossible. With the process according to the invention, the noise can be smoothened out without causing losses in the real peak intensity. It is then possible to sequence the protein chain by additional amino acid components without the need for additional apparatus.

In an analog manner, the integral extinction differences (iED) diagrams are used.

$$\int_{\lambda_1}^{\lambda_2} \Delta E_\lambda(t) \cdot d\lambda \text{ vs. } \int_{\lambda_3}^{\lambda_4} \Delta E_\lambda(t) \cdot d\lambda$$

The variations of the method according to the invention may also be used when the basis line as a function of the wave length drifts with time. By determining the time dependent values of the basis lines ($E_{80}{}^B(t)$) for example, using polynams $\Delta E_\lambda(t)$ can be defined as follows:

$$\Delta E_\lambda(t)=E_\lambda(t)-E_\lambda(t)^B(t)$$

In this way, "corrected ED"—or respectively "corrected IED diagrams" are constructed with which peak purity can be tested also in this case.

As a result, the great advantage of the various integral E-diagrams (iE) is combined with the basic inventive concept wherein a clear peak analysis is possible with increased detection sensitivity and with the elimination of classical disturbance factors such as basis line drift. This is achieved with only slightly higher calculation needs, which, however, can be easily accommodated by computers.

Double and Multiple Peaks

Systematic deviations from the straight lines were found when, in the curves to be analyzed as provided by the chromatogram or the electrogram, several ($s \geq 2$) components become apparent spectrographically. In these cases, it is recommended to use the EDQ diagrams which will be described further below.

If two or several components are not fully separated during the chromatography or the electrophoresis, double or multiple peaks can be formed. Also, quasi-simple peaks with shoulders have been observed. In order to determine whether two or several components were examined spectroscopically, in accordance with the invention EQ-, EDQ- integral EQ- and integral EDQ diagrams may be used.

Figure 2:
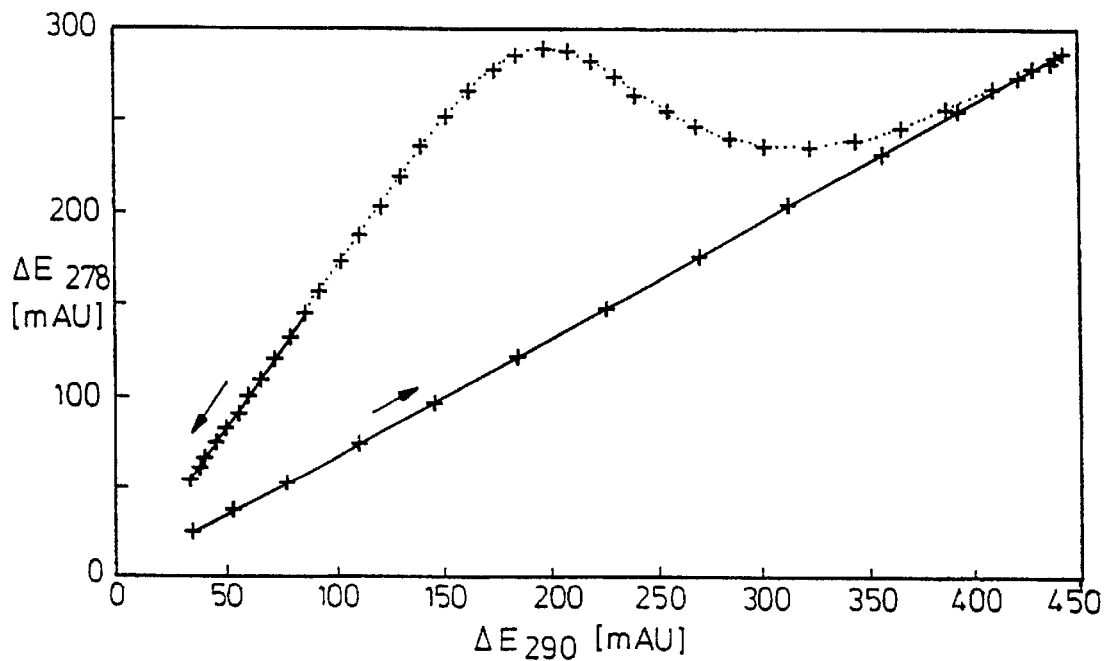
FIG. 2 shows an extinction difference (ED) diagram and, FIG. 3 shows an extinction difference-quotient (EDQ) diagram, wherein the quotients of, in each case, two extinction differences of different wave lengths are plotted with respect to each other. The parameter is the time in each case.

This will be explained on the basis of the following measurement example (FIG. 2).

Two Compounds are not Fully Separated in the Separation Procedure

The example relates to a mixture of Epicatechin and chlorogenic acid (two related flavonoids). A $C_{18}$-HPLC column was used. Methanol (40%) and water as well as acetic acid (1%) were used as the eluation medium. Peak detection occurred by means of a diode array spectrometer.

At the beginning of the chromatographic process, the first component is clearly separated from the second component. However, toward the end, the components are no longer separated. At the end, the concentration ratio of the two components is almost constant. Since, altogether, both components appear spectroscopically differently, characteristic E-, ED-, iE-, iE- and iED diagrams are obtained. Although in the example the simple ED-diagram is used, the principle of such a diagram applies in an analog manner for the EDQ—and all integral diagrams.

The ED diagram is based on the original measurement values ($E_{ijk}$ with K=0). At the rate at which the chromatographic peak is developed, the measurement points appear along a straight line beginning at the zero point (inclined upward arrow in FIG. 2). This linear area of the ED-diagram is more clearly apparent the more complete the separation of the first component from the second component is. If, during the chromatographic process, the concentration of the first component becomes smaller after reaching a maximum value without the second component becoming spectroscpically apparent, the points return toward the zero point on the original straight line for a certain distance. In FIG. 2, all the upward points and some of the return points are disposed on a straight line. The inclination of this straight line then has a value which, with the wavelength i and j, is $$\frac{\Delta E_i}{\Delta E_j} = \text{constant} \quad (= 1 \ EDQ \ \text{value})$$

Then the second component becomes apparent during the chromatographic process. This means for the ED-diagrams that the points move away from the original zero point straight line (=nonlinear extension of the return curve in FIG. 2). This has the following consequences:

On the basis of the ED diagrams, it can be immediately recognized, after which retention time the second component is spectroscopically examined. It is therefore possible to collect the first component in a pure form up to that point.

When the second component appears, the following points in the EDQ diagram leave the starting point and follow another straight line.

II EDQ-diagrams and Their Integral Analogs

The quotients $\Delta E_i/\Delta E_j$ are used for the construction of EDQ diagrams. FIG. 3 represents an EDQ diagram for the component mixture described in connection with FIG. 2. For this purpose, the quotients of different wavelength combinations $$\frac{\Delta E_i}{\Delta E_j} \text{ and } \frac{\Delta E_k}{\Delta E_j}$$

are plotted over one another (3 wavelengths i, j, k). The geometric interpretation of this pair of quotients are the inclinations of exemplary straight lines in the diagrams $\Delta E_1$ over $\Delta E_j$. (FIG. 2) and $\Delta E_k$ over $\Delta E_j$.

At least two ED diagrams are required in order to construct an EDQ-diagram (FIG. 3). The two upward straight lines of two ED diagrams generate one point in the corresponding EDQ diagram.

If the EDQ values for the points, which are not disposed in the linear beginning range with the ED diagrams placed in a ratio, and these values are plotted in the corresponding EDQ diagram, a straight line is obtained.

When the second component appears in the example described herein the resulting EDQ points are also arranged along a straight line as seen in FIG. 3. In order to recognize deviations, several wavelength combinations are tested. If exclusively straight lines are obtained, it is safe to assume that the chromatography peak includes exactly two components (s=2) as it is described in the example.

With this as well as other examples, it could be shown with high certainty that exclusively two component peaks were spectroscopically examined.

Generally, in the peaks of the chromatograms and the electrograms, exclusively two components (s=2) are only then recorded spectroscopically if the spectral measurement points are disposed on straight lines in the EDQ-diagrams. Practically, it is advantageous to select wavelengths, which are as much as possible distributed in the spectra. Again, 5–10 wavelengths are sufficient in order to obtain clear results. The process is completely transparent also for the user. Only differences and quotients are formed. This can be achieved in a simple manner.

For forming the quotients, various expressions may be utilized such that, in addition to the EDQ diagrams, extinction quotients, (EQ)-, integral EDQ- and integral EQ- diagrams can be constructed. The EDQ-diagram is directly converted to the EQ-diagram if the reference values $E_{ijk}$ are zero so that, for the extinction difference $\Delta E_{ij}$ are zero so that for the extinction difference $\Delta E_{ij}(t)$ the following applies:

$$\Delta E_{ij}(t) = E_{ij}(t) - E_{ijk} = E_{ij}(t)$$

In accordance therewith for the EQ diagram the plotting points are produced:

$$\frac{E_i}{E_j} \text{ vs. } \frac{E_k}{E_j}$$

For the integral EQD diagrams, the respective quotients are formed and plotted one over the other:

$$\frac{\int_{\lambda_3}^{\lambda_4}\Delta E_\lambda \cdot d\lambda}{\int_{\lambda_1}^{\lambda_2}\Delta E_\lambda \cdot d\lambda} \quad vs. \quad \frac{\int_{\lambda_5}^{\lambda_6}\Delta E_\lambda \cdot d\lambda}{\int_{\lambda_1}^{\lambda_2}\Delta E_\lambda \cdot d\lambda}$$

In an analog manner, the integral EQ diagram (iEQ) is used.

For the integration interval $\Delta\lambda(\lambda_2-\lambda_1, \lambda_4-\lambda_3, \lambda_6-\lambda_5)$ a difference value of about 4–10 nm has been found suitable with diode array spectrometers in the area of UV-VIS.

A particular advantage of the invention with the use of the integral iEQ and iEDQ diagrams resides in the fact that, for example, chromatograms can be evaluated to obtain important information even if the spectra include a large amount of noise and/or the individual components are only slightly different. With the integration formation, unclear data can be made visible; the dampening of the noise signals occurs without losses in the real peak.

Differential Diagrams.

Vice versa, instead of the values obtained by integration, differential values obtained by differentiation may be placed in relation to each other.

In this way, a series of differential (d-) diagrams are obtained which are formed analog to the normal and integration values as dE, dED and/or dEDQ values. This derivative technique has the advantage of an even clearer distinction of the peak components, but it also amplifies the noise of the base lines.

Smoothing Out of the Measurement Curves

In many cases, it is advantageous to smoothen thin measurement data by way of polynomes before the E-, $EDQ_1$, iE, iED, iEDQ, dE, dED- and dEDQ diagrams are constructed.

III Generalization of the process according to the invention for multi-component systems of any spectroscopic origin.

With peaks having multi-compositions (s-components) EQ- and EDQs diagrams and their integral forms can be constructed.

Generally, in the EDQs diagram, the following plot is constructed ($\Delta E\lambda_i = \Delta E_i$):

| | | |
|---|---|---|
| $\Delta E_1$ | $\Delta E_{11}$ | $\Delta E_{1(s-2)}$ |
| $\Delta E_2$ | $\Delta E_{21}$ | $\Delta E_{2(s-2)}$ |
| . | . | . |
| . | . | . |
| . | . | . |
| $\Delta E_{(s-1)}$ | $\Delta E_{(s-1)1} \ldots$ | $\Delta E_{1(s-1)(s-2)}$ |
| | \|D\| | |
| $\Delta E_{(s+1)}$ | $\Delta E_{(s-1)1}$ | $\Delta E_{(s+1)(S-2)}$ |
| $\Delta E_2$ | $\Delta E_{21}$ | $\Delta E_{2(S-2)}$ |
| . | . | . |
| . | . | . |
| . | . | . |
| $\Delta E_{(s-1)}$ with | $\Delta E_{(s-1)1} \ldots$ | $\Delta E_{(S-1)(s-2)}$ |
| $\Delta E_s$ | $\Delta E_{s1}$ | $\Delta E_{s(S-2)}$ |
| $\Delta E_2$ | $\Delta E_{21}$ | $\Delta E_{2(S-2)}$ |
| . | . | . |
| . | . | . |
| . | . | . |
| $\Delta E_{(s-1)}$ | $\Delta E_{(s-1)1} \ldots$ | $\Delta E_{1(S-1)(s-2)}$ |

Herein the quotients of determinations of the order (s–1) are plotted one over the other in a two-dimensional diagram. Herefor extinction differences of at least (s+1) wavelengths must be included in the evaluation. The doubly indexed values $\Delta E_{mn}$ (m=1, 2 ... (s+1)$_1$ n=1, 2 ... (s–2) refer to experimentally determined extinction differences of (s–2) selected measurement values with (s+1) wavelengths. As a result, from the values $\Delta E_1$ and $\Delta Em_n$ matrices are formed whose determinants, after the formation of quotients, lead directly to the EDQs- diagrams.

In the EDQs diagrams straight lines are generated if, in the peak of the chromatogram, or respectively, electrogram being examined, exactly s components are differentiated. Also, in this case, in practice different EDQ diagrams are constructed by variation of the wavelengths. Straight lines extending parallel to the axes of the coordinates and through the origin are to be disregarded as abnormal cases.

The complete process scheme for the recognition and the disentanglement of multi-component peaks is summarized in tables 1 and 2.

The analysis and separation processes according to the invention are completely independent of the knowledge of the spectra and/or the extinction coefficients of individual components. The computations, including the resolution of the matrices, are performed by computer. The diagrams can be re-called in all states of the analysis and can be made visible, whereby the operator or user of an instrument based on the process can input decisions if the process does not follow the normal routine. The user has an instrument, which is transparent in all phases of its operation which is highly controllable and which can learn.

Even highly problematic separation problems can be solved in this way rapidly, inexpensively and with little efforts.

In this regard, below two particularly characteristic application examples of high actuality are presented. They concern problems which need to be solved urgently and which are unsolved at the present state of the art or which can presently only be solved by complicated and expensive methods.

Drug control in the presence of marking substances.

It happens more and more frequently that the use of illegal drugs is masked by the additional ingestion of a harmless substance. The harmless substance occupies a peak position in the given analysis procedure prescribed by law, which peak position is also occupied by the particular drug. In this way, the analytical drug control can be circumvented. The analysis has no legal proof capability. At least there is no clear proof. At the present state of routine checks, this situation remains unsolved. The present invention solves this problem by providing a clear answer.

With the progressing computer-supported peak analysis, starting with simple E diagrams and continuing with ED-, EDQ-, EDQs diagrams and further with their integral and differential analogies up to the combination thereof with one another, it is basically possible to identify even quasi-identically located peaks as a group of peaks. In this way, an intended or unintended circumvention of the legal checks can be eliminated and the legal proof capability is re-established. In addition, the routine analysis apparatus presently in use can be employed. Only a dispositive for the automatic peak analysis according to the invention must be added.

Detection of viral and subviral molecules and their distinction from a multitude of pathogenic and cell internal components.

The increasing contamination of the whole world by new viruses, viroids, subviroids and countless intra- and extracellular transition forms between them (for example, satellites, subgenomic segments, pseudoviruses, transposones, retro-tranpasones, plasmides) represents a dangerous situation not encountered earlier.

Numerous microorganisms are highly pathogenic in human veterinarian and phytosanitary areas, that is, they modify the behavior of normally harmless microorganisms such that also these microorganisms become harmful to humans and animals ("killer bacteria").

Included in this group are microorganisms of neurodegenerative pathologies such as the Creutzfeldt-Jacob-disease, of BSA and scrapie, and microorganism, which, like many others, have not been detected so far. It is the object to separate the respective microorganisms from a soup of cell-internal quasi-identical nucleic acids, initially for the purpose of scientific discovery and later for routine diagnoses of the respective diseases.

Because of their insignificant differences, all these molecules appear with the various detection methods in the same peak, which furthermore cannot be distinguished from the respective peak of non-infectious cell material.

Because of such difficulties, for example, the discovery of the viroids by T.O. Diener was delayed by years until they could be made visible by electron microscopy as individual dumbbell-shaped particles. This method, however, is expensive and time-consuming. Furthermore, it is not very promising for infectious agents in the animal and human areas since, at the present state of the art, it appears to be impossible, that a corpucular individual existence of the investigated viroid-analog nucleic acids in the animal cells can be made visible.

The discovery and diagnosis can be expected only from chromatographic and electrophoretic separation methods by determining the presence or absence of additional microorganism molecules in a multi-composition peak. The absence of a precise peak—fine analysis is believed to be the reason for the fact that it has been impossible so far to find the primary microorganism causing, for example, BSE, that is, to identify it in a soup of quasi-identical normal cellular nucleic acids. It is characteristic for the undeveloped state of the art that, at this time, the easily identifiable degenerated Prion proteins are viewed as the cause of the disease. It is pointed out however that Prion proteins are, in accordance with the molecular-biological logic and the diagnosis the visible final result, but not the cause of the pathogenese and can possibly only function as auto-catalyzing co-factors in a disease process already under way.

In the way already described, the process according to the invention permits to overstep the technical limits also in this case: multi-composite detection peaks caused by quasi-identical molecules or even by different stable melt isomer forms of one and the same nucleic acid (for example, a viroid) can be finely separated into their individual components.

Depending on the degree of difficulty of a given case, the peak analysis is advanced with increasing perfection. The number of parameters, the combination and the organization of the diagrams are further developed until each individual peak component appears as a single phenomenon and can be identified.

Particularly, the presence of microorganism molecules from infected material which are not present in the normal non-pathogenic cell material can be determined. This applies to scientific discovery processes as well as later to medical routine diagnostics.

Also, the various melt isomers of a finally identified microorganism nucleic acid can be distinguished from one another and recognized as individual species. They provide an indication whether the respective microorganisms are lightly or highly virulent or whether they are non-pathogenic.

The disease process resulting therefrom can be prognasticated. The effectiveness of possible medicines can be more rapidly estimated without having to wait for months or years for the appearance or the non-appearance of the slowly progressing lethal syndromes.

The identification of not or slightly pathogenic microorganisms is of particular interest:

They permit in certain cases a positive diagnosis: extremely long incubation periods, no outbreak of the disease during life expectancy.

They inspire their use as non-immunogenous innoculation for example against BSE, since these molecules, by incompatibility occupation of the active centers in the cell mechanism, inhibit access to virulent organisms appearing at a later time.

This is another example how, with the process according to the invention numerous methods in medicine and in many other areas can be advanced beyond their limits set by the present state of the art and unexpected perspectives can be opened up.

What is claimed is:

1. A process for determining the number of components involved in the formation of peaks, bands and signals which for purposes of analysis and substance separation, are obtained in spectrograms, where energy correlated measurement values increase as a function of an evolving parameter, and again decrease, said process comprising the following steps:

a) determining four different energy-correlated measurement values with at least three evolving parameter values, b) forming three differences from the respective four energy-correlated measurement values which belong to the same evolving parameter, c) forming two quotients from the respective three differences, and d) plotting the two quotients, one over the other, in a diagram whereby a point is obtained if there is only one component, a straight line is obtained if there are two components, and a curve is formed if there are more than two components responsible for the formation of the peaks, bands or signals.

2. A method according to claim 1, wherein additionally four respective measurement values are used with one or several additional parameter values.

3. A method according to claim 2, wherein, with a curve appearing in the diagram, for each parameter at least one additional measurement point is selected and wherein, instead of the quotients which represent determinants of a first degree, determinants of a second or higher degree are formed from the respective quotients which are plotted over one another whereby three or more components can be clearly recognized.

4. A method according to claim 1, wherein integrals of the energy-correlated measurement values are used.

5. A method according to claim 1, wherein differentials of the energy-correlated values are used.

6. A method according to claim 1, wherein a column is used for obtaining the spectrogram and wherein the evolving parameter is the retention time of said column, and a corresponding optical measurement value, the extinction differences and extinction differences quotient diagrams or, respectively, their integral analogs or their differential values are constructed and integrated into the determining process.

7. A method according to claim 1, wherein the measurement value, which increases and decreases with the evolving parameter, is any one of an additional spectrometric value comprising fluorescence intensity, rotational angle, reflection capability, ellipticity quantitatively measured NMR-intensity, x-rays, and γ-radiation.

* * * * *